United States Patent [19]

Yoshida

[11] Patent Number: 4,776,466
[45] Date of Patent: Oct. 11, 1988

[54] SURFACE INSPECTION APPARATUS

[75] Inventor: Hajime Yoshida, Tokyo, Japan

[73] Assignee: Hajime Industries, Ltd., Tokyo, Japan

[21] Appl. No.: 86,249

[22] Filed: Aug. 13, 1987

Related U.S. Application Data

[63] Continuation of Ser. No. 772,358, Sep. 4, 1985, abandoned.

[30] Foreign Application Priority Data

Oct. 24, 1984 [JP] Japan .................................. 59-223652

[51] Int. Cl.$^4$ ............................................. B07C 5/342
[52] U.S. Cl. ................................ 209/565; 209/576; 209/701; 209/939; 356/428; 358/106
[58] Field of Search ........ 209/522, 524, 526, 564–566, 209/576, 588, 936, 939; 358/106; 356/240, 428; 198/415

[56] References Cited

U.S. PATENT DOCUMENTS

| | | | |
|---|---|---|---|
| 3,799,736 | 3/1974 | Palladino | 198/415 X |
| 4,074,130 | 2/1978 | Messman et al. | 356/428 X |
| 4,280,624 | 7/1981 | Ford | 209/939 X |
| 4,376,951 | 3/1983 | Miyazawa | 209/939 X |
| 4,474,295 | 10/1984 | Braschos | 209/653 |
| 4,476,981 | 10/1984 | Yoshida | 209/653 X |
| 4,493,420 | 1/1985 | Dennis | 209/939 X |
| 4,549,205 | 10/1985 | Misaki et al. | 209/939 X |
| 4,582,201 | 4/1986 | Taniguchi et al. | 209/701 X |

FOREIGN PATENT DOCUMENTS

| | | | |
|---|---|---|---|
| 0216881 | 3/1958 | Australia | 198/415 |
| 0129940 | 1/1985 | European Pat. Off. | 209/565 |
| 0057938 | 5/1981 | Japan | 356/426 |

Primary Examiner—Robert B. Reeves
Assistant Examiner—Scott H. Werny
Attorney, Agent, or Firm—Bauer & Schaffer

[57] ABSTRACT

Objects to be inspected are transferred successively in one direction on a conveyor and irradiated by a light source and photosensed by a single optical image sensor only, such as a video camera. The optical image sensor is so arranged that it simultaneously photosenses a plurality of the successively transferred inspected objects, and the conveyor is so constructed that during the period in which the objects pass through the visual field of the optical image sensor, the objects are rotated so that their entire round inspected surfaces are all respectively photosensed by the optical image sensor. The video signal from the optical sensor is supplied to an inspection device which periodically samples the video signal in synchronization with the shift movements of the objects, and judgment signals therefrom are respectively supplied to the parallel input terminals of a shift register, the number of which is the same as that of the number of objects in the visual field and at the same time a shift pulse synchronized with the movement of the objects is supplied to the shift register whereby it produces an output signal corresponding to the defective object to cause rejection of the defective object.

4 Claims, 2 Drawing Sheets

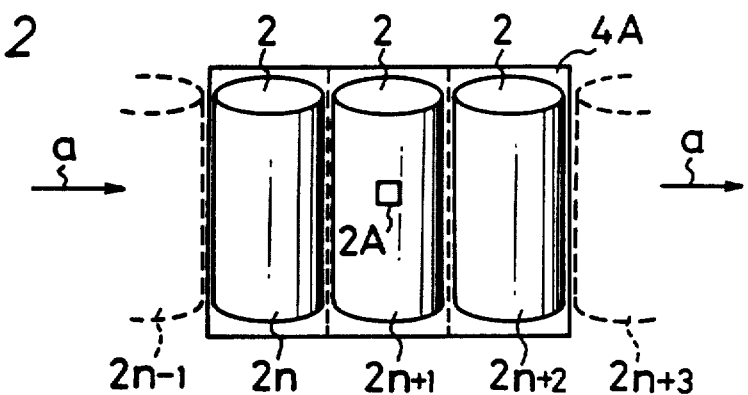
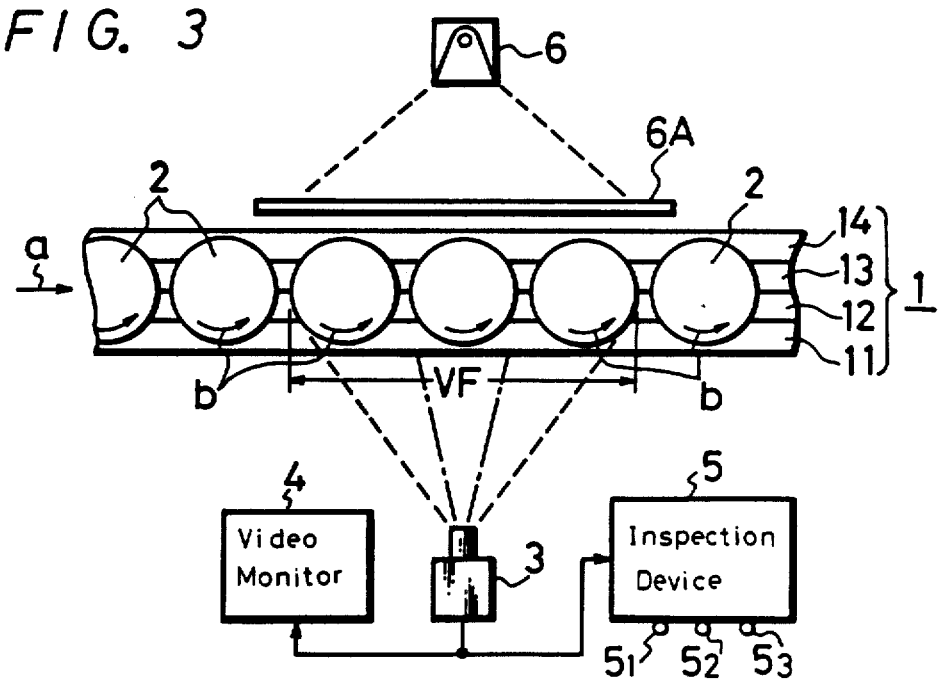
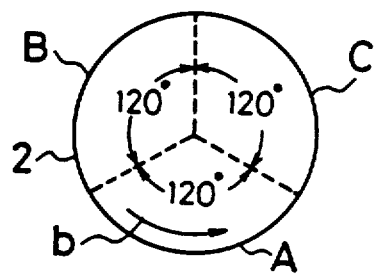

SURFACE INSPECTION APPARATUS

This is a continuation of Ser. No. 06/772,358 filed Sept. 4, 1985 now abandoned.

BACKGROUND OF THE INVENTION

1. Field of the Invention

The present invention relates generally to an inspection apparatus, and more particularly to a surface inspection apparatus which can automatically inspect for defects in the surfaces of objects to be inspected as they are carried along on a continuous belt conveyor or the like, by the use of a single optical image sensor or the like.

2. Description of the Prior Art

Recently, many types of devices have been proposed for automatically inspecting objects, as a replacement for the personal inspection conducted by the human eye. In these devices, the appearance or surface of the objects are viewed through optical image sensors such as video cameras or the like to produce video signals thereof and then such video signals are processed in electronic circuitry or the like to automatically determine whether or not a defect in the objects exist.

However, in the above known prior art inspection devices, the video camera is normally fixed and its visual field is limited to one direction. Accordingly, when an object to be inspected is a cubic body such as a cup or the like, its entire round surface cannot be inspected at one time.

Alternatively, methods of inspection have been suggested that use a number of video cameras to view a single object to be inspected so that the inspected object may be simultaneously inspected from several different directions at once. However, this method contains a defect in that it necessitates a number of video cameras as well as multi processing circuits which make the system expensive and which also requires a large inspection space.

Further, proposals have been made to use one video camera and to stop the cubic object, such as a cup at the inspection position, and thereafter rotating the object, so that the inspection area is changed. By thus repeating the inspection several times, the entire round surface of the object will be inspected. This method requires a long time to inspect a single object which makes it impossible to adopt this method to the inspection of a plurality of objects, such as cups or the like, that flow on a belt conveyor.

OBJECTS AND SUMMARY OF THE INVENTION

Accordingly, it is an object of the present invention to provide an inspection apparatus free from the disadvantages inherent to the prior art.

It is another object of the present invention to provide a surface inspection apparatus which employs a single optical image sensor and can inspect all the surface of an object to be inspected as the object is fed onto a conveyor.

It is a further object of the present invention to provide a surface inspection apparatus which can inspect an object fed onto a conveyor and can automatically remove an object from the conveyor when the object is defective.

According to an aspect of the present invention, there is provided an inspection apparatus comprising:

(a) a conveyor for transporting objects to be inspected, said objects being aligned in successive uniformly spaced relationship to each other and moving at a constant rate of travel, (b) a single optical image sensor having a field of vision including a plurality of said objects and producing a video signal containing all of the objects in said field of vision, (c) means for rotating said objects on said conveyor at least during the period in which each object is within the field of vision of said optical image sensor, so that the entire surface of said object is successively visible to said optical image sensor at different locations within said field of vision, (d) a pluse signal generator for producing a timing pulse signal in direct synchronism with the movement of said object on said conveyor, (e) an inspection device having an input terminal receiving said video signal from said optical image sensor, and processing means responsive to said timing pulse to periodically sample said video signal to determine from said sample whether or not each of the objects represented in said video signal contains a defect and to produce corresponding output judgment signals indicative of the condition of each of the objects contained in the sample, (f) a shift register having a plurality of parallel input terminals adapted to respectively receive one of the judgment output signals from said inspection device, said shift register being responsive to said timing pulse signal to shift said judgment signals sequentially to an output terminal, whereby every time a timing pulse signal is supplied to said inspection device, simultaneous determination is made of the video signals corresponding to the plurality of parallel input terminals of said shift register while the pulse signal is supplied to said shift register so that said shift register shifts the judgment signals toward its output terminal in synchronism with the movement of said objects through said field of vision.

These, as well as other objects, features and advantages of the present invention will become apparent from the following description taken in conjunction with the accompanying drawings through which the like references designate the same elements and parts.

BRIEF DESCRIPTION OF THE DRAWINGS

FIG. 2 is a plan view of the picture screen of a video monitor;

FIG. 3 is an enlarged view of a part of FIG. 1; and

FIG. 4 is a schematic diagram of a top plan view of an object at the inspection station.

DESCRIPTION OF THE PREFERRED EMBODIMENT

Figure 1:
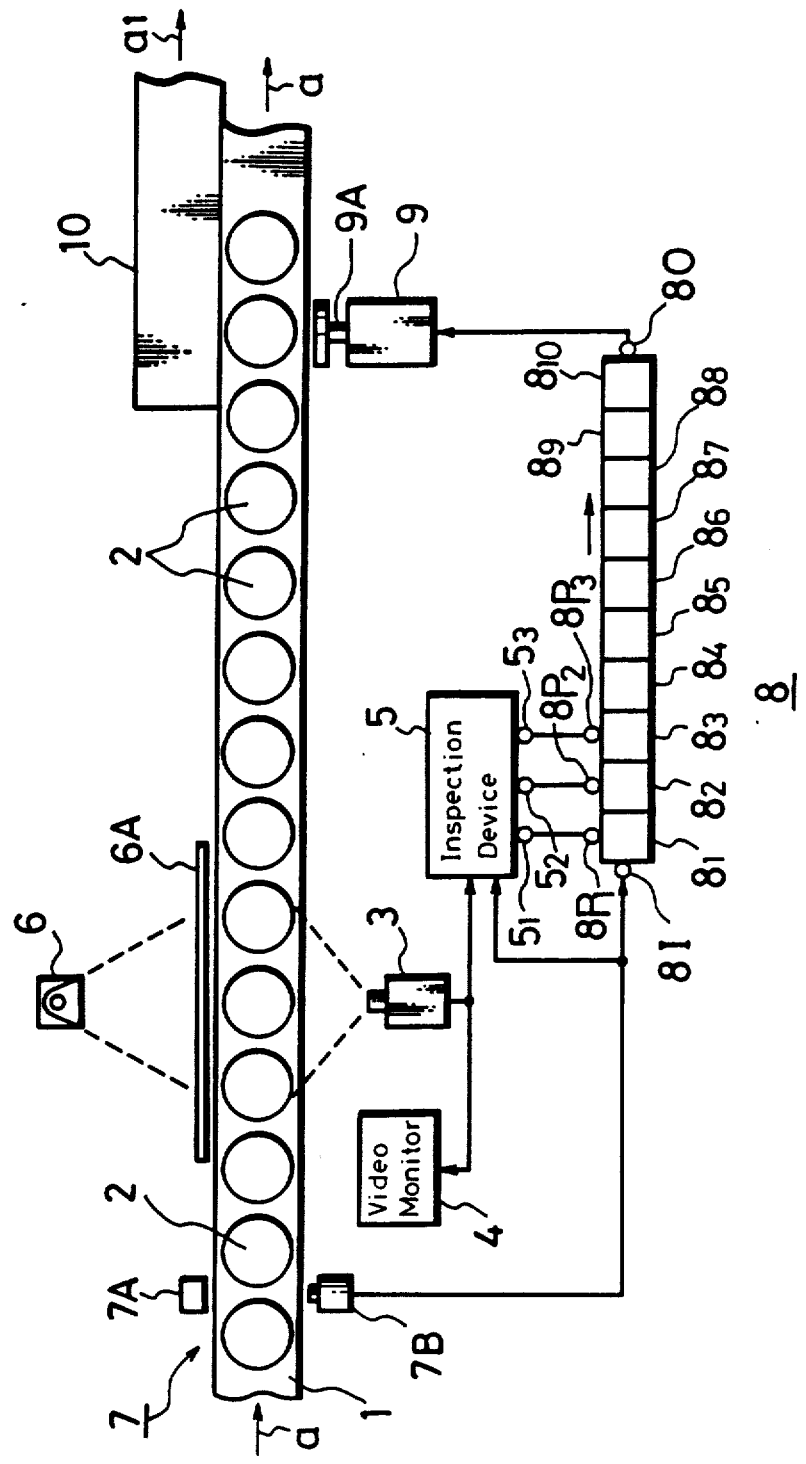
FIG. 1 is a schematic block diagram of the inspection apparatus according to the present invention.

An example of the invention with the features as above mentioned will be explained hereunder in reference with the attached drawings.

In FIG. 1, a conveyor 1 such as a belt conveyor or the like is shown, on which objects 2, to be inspected, here illustrated as transparent cups, bottles or the like, are conveyed continuously at a substantially constant speed and at a predetermined distance from each other in the direction indicated by an arrow a. A single optical image sensor 3, such as a video camera is positioned so that it has a field of vision in which a plurality, in this example three, of the objects 2 are simultaneously photosensed. A video monitor 4 receives the video signal from the video camera 3 and reproduces the images of the sensed objects 2 (three cups) on its picture screen. Simultaneously, the video signal is fed to an inspection device 5 which includes electronic processing circuitry which processes the video signal from video camera 3 to determine the existence of any defect on the surface of the objects 2 and then deliver output signals corresponding thereto (in the case of good, an output signal "0" and in the case of bad, an output signal "1". A light source 6 is positioned so that it irradiates the objects 2 and the light passing therethrough is picked up by the video camera 3. An optical transmission diffusor 6A is placed between the object 2 and the light source 6 so that the light from the light source 6 uniformly irradiates over a wide range a plurality of objects on the conveyor and in this case, at least, three objects 2.

In the example as shown on FIG. 1, the inspected object 2 is a transparent glass cup as aforementioned, and the light source 6 is positioned at the counter side to the video camera 3 in relation to the object 2 so that the light from the light source 6 passes through the objects 2 to be picked up by the video camera 3.

Further, as seen in FIG. 1, an optical beam generator 7A such as a light emission diode, and a light receiver 7B such as a photo cell are placed on opposite sides of the conveyor upstream from the video camera 3 to form a pulse generator, generally depicted by the numeral 7. The pulse generator 7 is arranged so that even though the light beam is constantly emmitted from the beam generator 7A, a timing signal is produced in the receiver only when an object 2 passes between the two elements 7A and 7B and the light beam is shielded (or weakened). In other words, whenever an object 2 passes through the pulse generator 7, a timing pulse signal is generated by the photo cell element 7B. This timing pulse signal is supplied to the inspection device 5 as a second input. The inspection device 5 is responsive to each timing pulse signal to sample the video signal from the video camera 3, which in this case means the simultaneous processing of the video signals of three successive objects 2 to provide a judgment signal for each and delivers separate judgment signals for each of the respective objects 2 at three output terminals $5_1$, $5_2$ and $5_3$. The output signals $5_1$, $5_2$ and $5_3$ are respectively fed to parallel input terminals $8P_1$, $8P_2$ and $8P_3$ of a shift register 8, having a plurality of registers, e.g., $8_1$ to $8_{10}$.

The shift register also receives the pulse signal from the photo cell 7B in an input terminal 8I. The pulse signal thus acts as a shift pulse by which the aforementioned judgment signals are shifted one step each in sequence through memory cells $8_1$ to $8_{10}$ towards the output terminal 80 of the shift register 8 for each shift pulse supplied to the input 8I.

A rejection device 9 for removing a defective product is located at a predetermined place down stream on the conveyor 1 relative to the video camera 3. The rejection device 9 is driven by an appropriate output signal from the output terminal 80 of the shift register 8 (the driving signal is preferably a binary output "1"; signal "0" not acting to drive the rejection device 9). The rejected objects 2 are pushed onto an auxilliary conveyor 10, for defective products, provided adjacent the far side of conveyor 1, and moving in the direction shown by the arrow A1.

An example of the operation of the surface inspection apparatus according to the present invention is illustrated in FIGS. 2 through 4. Here, three objects 2 of a continuous line of conveyed objects, such as three cups made of transparent glass are simultaneously inspected. In FIG. 2 the three objects 2 are shown on the picture screen 4A of the video monitor 4 at a certain point of time at which the respective object images are positioned at three successive locations $2_n$, $2_{n+1}$ and $2_{n+2}$ relative to the moving conveyor 1. It is noted that the objects 2 at the conveyor position $2_{n-1}$, $2_{n+3}$ are not within the visual field of the video camera 3, and accordingly their images are not reproduced on the picture screen 4A of the video monitor 4.

The objects 2 are rotated while on the conveyor 1 so that during the time period that each of the objects 2 pass through the visual field of the video camera 3, all of the surface (inspected surfaces) of each object that should be inspected is presented to the video camera so that they can be photosensed by the video camera 3. Thus, each of the objects 2 is roughly rotated for one revolution while it passes through the visual field of the video camera 3. To this end, as shown on FIG. 3, the conveyor 1 comprises a continuous belt which is divided into four respectively parallel strips 11, 12, 13 and 14, each having a transfer speed, in the direction of arrow a, which is slower sequentially from strip 11 to 14. Thus, each of the objects 2 can be rotated about their vertical axis while in the visual field of video camera 3, i.e., the distance VF, so that all of the surfaces of the object may be photosensed by the video camera 3.

Returning to FIG. 2, when the objects 2 that are positioned at the three successive locations $2_n'$, $2_{n+1}$ and $2_{n+2}$ are simultaneously photosensed by the single video camera 3, the rotation phase differences of the three objects 2, at successive locations $2_n'$, $2_{n+1}$ and $2_{n+2}$ are about 120 degrees to each other. Consequently, the single video camera 3 is capable of sequentially sensing the entire peripheral surface of the object as it passes successively through the three locations $2_n'$, $2_{n+1}$ and $2_{n+2}$.

Although the video camera 3 continuously views the objects 2, the video signals from the video camera 3 are not continuously processed by the inspection device 5, but rather are periodically sampled. The video signal is sampled in response to the timing pulse signal so that only those specific positions of the video signals from the video camera 3 when the object exists at the three locations $2_n'$, $2_{n+1}$ and $2_{n+2}$. Needless to say, when a particular object is at location $2_n'$, two prior objects are at locations $2_{n+1}$ and $2_{n+2}$, respectively and the video signals of these objects, out of rotational phase, are sampled and processed simultaneously with the video signal of the object at location $2_n$, by feeding such video signals separately but simultaneously to the parallel input terminals $8P_1$, $8P_2$ and $8P_3$ of the shift register 8, as above described.

In order to process the specific video signals from the video camera 3 when each of the objects 2 exists at locations $2_n'$, $2_{n+1}'$ and $2_{n+2}'$ the pulse signal from the photo cell 7B is supplied to the inspection device 5 and only when this pulse signal is supplied thereto, does the inspection device 5 supply the judgment signals to the shift register 8.

Thus, the outer surface of the object is inspected at three locations where the rotation phases are different, as can be seen in FIG. 4. In FIG. 4, the object is illustrated in cylindrical form and shown in plan as divided into three equal portions (at 120 degree intervals) such as A, B, C. Assuming that the photosensed range of the object 2 at location $2_{n+2}$ is the portion A, the photosensed ranges of the object at locations $2_{n+1}$ and $2_n$ are portions B and C. In other words, while each of the objects passes through the visual field of video camera 3, making one rotation, the video camera 3 can view three equally split portions A, B, C for processing at the inspection device 5.

Assuming now, that a certain object 2 has a defect such as crack 2A in the sector corresponding to the portion B as shown on FIG. 2. This object at location $2_n$, has only its portion A photosensed so that the video signal in response to this position does not cause any defect output signal from the inspection device 5 (output signal "0"). However, at the next position $2_n$, the portion B which contains the defect 2A is photosensed and a video signal including the defect 2A is sent from the video camera 3 to the inspection device 5. Consequently, the inspection device 5 will produce as an output a defect signal (signal "1") corresponding to the location $2_{n+1}$. Further, when the cup 2 advances to the next location $2_{n+2}$' the portion C of cup 2 is photosensed, and therefor as in the case of photosensing the portion A, the inspection device 5 does not produce as an output a defect signal and actually outputs a signal "0" corresponding to location $2_{n+2}$.

Such signal processsing is conducted with regard to each cup 2 that enters the visual field VF of the video camera 3 successively and consecutively at a predetermined time interval.

The inspection device 5 may be of any arrangement so long as it is a type where, for example, the analog video signals from the video camera 3 are converted into digital signals via an A/D (analog-to-digital) converter. Such digital signals are electrically processed by microprossors or the like and whenever there is an abnormality responsive to a defect contained in the input video signal, a digital output is produced.

In the example of the invention as above explained, the inspection device 5 has, as shown on FIG. 1, three output terminals $5_1$, $5_2$ and $5_3$ corresponding to the locations $2_n$, $2_{n+1}$ and $2_{n+2}$, respectively and their outputs (judgment outputs) resulting from the video signal processing at the respective locations, appear at the output terminals $5_1$, $5_2$ and $5_3$.

The shift register 8, as shown on FIG. 1, comprises a plurality of, in this example, ten memory cells $8_1$, $8_2$ . . . $8_9$, $8_{10}$ that are consecutively aligned and the output terminals $5_1$, $5_2$ and $5_3$ of the inspection device 5 are respectively connected to the parallel input terminals $8P_1$, $8P_2$ and $8P_3$ that are respectively mounted on the first, second, third memory cells $8_1$, $8_2$ and $8_3$.

Since one shift pulse is supplied to the input 8I from the photo cell 7B each time the object 2 moves for one step in the direction of arrow a, the judgment output signals from the output terminals $5_1$, $5_2$ and $5_3$ of the inspection device 5 that are supplied respectively to the memory cells $8_1$, $8_2$ and $8_3$ are shifted respectively for one memory cell only, towards output terminal 80 in synchronism with the shift pulse.

In the example shown in FIG. 1 since the shift register 8 is formed of ten memory cells $8_1$, . . . $8_{10}$, the timing by which the judgment output signal that is supplied to the first memory cell $8_1$ will appear at the output terminal 80 corresponds to the time for the object to be transferred downstream on the conveyor equivalent to ten object spaces. Therefore, by disposing the rejection device 9 downstream at the 10th object location on the conveyor 1 counting from the first object in the visual field of the video camera 3 and the rejection device 9 is driven by the signal that appears at the output terminal 80 of the shift register 8, the defective cup rejection timing matches the shift timing of shift register 8 to thereby positively reject only the defective object.

The rejection device 9, for example, can be of the solenoid type that is driven when the signal (signal "1") from the shift register 8 is received. On energization of the solenoid coil its rod 9A protrudes to push the defective object from the conveyor 1 to the rejection conveyor 10, after which it automatically retreats to the original position (as per status on FIG. 1) and maintains such standby status until the next signal "1" is received.

As a practical explanation, it will be assumed that a certain object 2 has the defect 2A only at its portion B as shown on FIG. 4, although it may have already been photosensed for its portion A by the video camera 3 at location $2_n$ as shown on FIG. 2. As a result of which no abnormal signal is contained in the video signal from video camera 3 corresponding to the location $2_n$. Therefore, a signal "0" is delivered from the output terminal $5_1$ of the inspection device 5 which is supplied to the first memory cell $8_1$ of the shift register 8 through its input terminal $8P_1$. When the object arrives at the next location $2_{n+1}$, the portion B which contains the defect 2A is photosensed, so that a signal "1" is delivered from the output terminal $5_2$ of the inspection device 5 which is supplied to the second memory cell $8_2$ through the input termianl $8P_2$.

At the next location $2_{n+2}$ the portion C of the cup 2 is photosensed, but since there is no defect in this portion C of the object 2, signal "0" is delivered from the output terminal $5_3$ of the inspection device 5, which is supplied to the third memory cell $8_3$ through the input terminal $8P_3$. Thereafter, the object 2 is transferred by the conveyor 1 in the direction of arrow a eventually arriving at the downstream location $2_{n+9}$ which is ten object spaces down from the first location $2_n$ (which is 9 object spaces down from location $2_{n+1}$, where the defect 2A was photosensed), and where the rejection system 9 is placed. The signal "1" that was supplied to the second memory cell $8_2$ of the shift register 8 has also just arrived at the output terminal 80 of the shift register 8, so that the rejection device 9 is driven by this signal "1" and the defective object is pushed from conveyor 1 to the rejection conveyor 10.

The shift register 8 is used to adjust the reject timing of the defective object 2, so that in response to the fixed installation location of the rejection device 9, the number of memory cells of the shift register 8 may be increased or decreased.

Further, while in the above described example the object 2 was rotated one revolution within the visual field of the video camera 3, during which time the surface defect inspection was conducted at 3 locations, each being turned for 120 degrees. Depending upon the type of objects inspected, for instance, in the case where the cups are made of transparent material as above mentioned, since the light from the light source 6 as shown in FIG. 1 passes through the object to enter the video camera 3, the video camera 3 will be able to simultaneously photosense two portions of the object in counter location to each other. Therefore, it will not be necessary to have a full rotation (360 degrees) of the cup within the visual field of the video camera 3. In other words, it is sufficient that in order to photosense that portion which cannot be initially photosensed at, for example, location $2_n$, the object need only be turned slightly. In this case, the construction of the conveyor 1 can be simplified.

It is also apparent that the number of objects which are to be inspected within the visual field that are simultaneously photosensed by the video camera 3 need not be limited to 3, but depending upon the resolution of the video camera and object size, it may be as few as 2 or 4 or more.

Further, while in the aforementioned example of the present invention, the light source 6 is placed at the opposite side of the video camera 3 relative to the inspected object 2, however when the inspected objects 2 are made of opaque material, the light source 6 may be placed on the same side as the video camera 3.

According to the present invention, all of the surfaces of a cubic object such as a cup to be inspected which cannot be inspected by a single optical image sensor such as a video camera, can be fully inspected by photosensing the object at a plurality of locations within the visual field of the single optical image sensor without disturbing the conveyance of the inspected object at all, and eventually the defective products can be rejected from the conveyor after the inspection. The above mentioned inspection, as well as defect product rejection are all conducted automatically.

In addition, without departing from the scope of the novel concepts of the present invention, it is apparent that any person skilled in the art may provide many variations and changes, so that the scope of the invention should be determined by the appended claims only.

I claim as my invention:

1. An inspection apparatus comprising:
    (a) a conveyor for transporting objects to be inspected, said objects being aligned in successive uniformly spaced relationship to each other and moving at a constant rate of travel;
    (b) a single optical image sensor having a field of vision including a predetermined plurality of said objects and producing a continuous video signal of all of the field of vision;
    (c) means for rotating each of said objects while being transported by said conveyor means within the field of vision, stepwise about their central axis successively through each of a plurality of locations corresponding to the number of objects within the field of vision, each stepwise rotation presenting a successive fractional part of the peripheral surface of said object to said image sensor at a successively corresponding location within said field of vision, so that each fractional part of the peripheral surface is sequentially visible to said image sensor;
    (d) a pulse signal generator for producing a timing pulse signal in direct stepwise synchronism with the traverse of said objects from location to location within the field of vision;
    (e) an inspection device having an input terminal receiving said video signal from said optical image sensor, and processing means responsive to said timing pulse to periodically sample said video signal to determine from said sample whether or not each of the fractional parts of the peripheral surfaces of each of said objects represented in said video signal contains a defect and to produce corresponding output judgement signals indicative of the condition of each of the objects contained in the field of vision;
    (f) a shift register having a plurality of parallel input terminals adapted to respectively receive one of the judgement output signals from said inspection device, said shift register being responsive to said timing pulse signal to shift said judgement signals sequentially to an output terminal so that every time a timing pulse signal is supplied to said inspection device, simultaneous determination is made of the judgement signals corresponding to the object at each of the successsive locations at that moment in said field of vision and the judgement signals are correspondingly supplied to the plurality of parallel input terminals of said shift register while the pulse signal is supplied to said shift register so that said shift register shifts the judgement signals toward its output terminal in synchronism with the movement of said objects through said field of vision; and
    (g) a rejection device connected to the output terminal of said shift register and located downstream from a first object in the field of vision by at least the distance equivalent to the length of the field of vision and said output terminal of said shift register is located downstream by a corresponding number of memory cells in said shift register, such that when the output signal from said shift register indicates a defective object, said rejection device is driven by this output signal to remove the defective object from said conveyor.

2. The inspection apparatus according to claim 1, in which said conveyor comprises a plurality of conveyor belts which move relative to each other at different speeds so as to cause the objects thereon to rotate.

3. A method for inspecting objects having a central axis and a peripheral surface comprising the steps of transporting, at a constant rate of travel, a succession of objects, in uniformly spaced linear alignment, past a single optical image sensor, having a field of vision consisting of a predetermined plurality of said object and producing a continuous video signal containing all of the objects traversing the field of vision, simultaneously rotating each of said objects located within the field of vision, stepwise about their central axis successively through each of the locations corresponding to the number of objects within the field of the vision each stepwise rotation presenting a successive fractional part of the peripheral surface of said objects to said image sensor at the corresponding location, so that as said object is transported through said field of vision the entire peripheral surface is sequentially visible to said image sensor and periodically processing said video signal at intervals in synchronism to the stepwise movement of said objects to determine any defect existing in each of the fractional parts of the peripheral surface visible at said interval to said image sensor and producing corresponding output judgement signals indicating the condition of said fractional part of each object subsequently at each location within said field of vision at said interval correlating each of said output judgement signals associated with each object to provide a series of composite signals each indicative of the condition of the entire periphery of a corresponding object.

4. The method according to claim 3, including the step of removing, from the objects transported in linear alignment, the object corresponding to a composite judgement signal indicating a defective condition.

* * * * *